(12) United States Patent
Locke et al.

(10) Patent No.: US 8,089,367 B2
(45) Date of Patent: Jan. 3, 2012

(54) METHOD AND APPARATUS FOR DETECTING CONSTITUENT CHANGES IN AN ENVIRONMENT

(75) Inventors: Edward P. Locke, Norfolk, VA (US); Thomas Clifford, Virginia Beach, VA (US); Robert B. Jeffers, Virginia Beach, VA (US); Julian E. Parker, III, Chesapeake, VA (US)

(73) Assignee: K & M Environmental, Inc., Virginia Beach, VA (US)

( * ) Notice: Subject to any disclaimer, the term of this patent is extended or adjusted under 35 U.S.C. 154(b) by 315 days.

(21) Appl. No.: 12/056,002

(22) Filed: Mar. 26, 2008

(65) Prior Publication Data
US 2008/0238700 A1    Oct. 2, 2008

Related U.S. Application Data

(60) Provisional application No. 60/908,563, filed on Mar. 28, 2007.

(51) Int. Cl.
*G08B 17/10* (2006.01)
(52) U.S. Cl. ............... 340/632; 340/540; 340/691.1
(58) Field of Classification Search .......... 340/632, 340/691.1, 541, 540
See application file for complete search history.

(56) References Cited

U.S. PATENT DOCUMENTS

| | | | |
|---|---|---|---|
| 4,864,462 A | 9/1989 | Madou et al. | |
| 5,512,882 A | 4/1996 | Stetter et al. | |
| 5,659,296 A | 8/1997 | Debe et al. | |
| 5,666,949 A | 9/1997 | Debe et al. | |
| 6,774,643 B2 | 8/2004 | Magill | |
| 6,783,989 B1 * | 8/2004 | Zakin | 436/104 |
| 6,842,009 B2 * | 1/2005 | Potter | 324/633 |
| 7,034,677 B2 * | 4/2006 | Steinthal et al. | 340/539.12 |
| 7,066,172 B2 * | 6/2006 | Pasternack | 128/202.22 |
| 7,115,362 B2 * | 10/2006 | Douglas et al. | 436/525 |
| 7,392,806 B2 * | 7/2008 | Yuen et al. | 128/205.27 |
| 7,775,975 B2 * | 8/2010 | Brister et al. | 600/309 |

OTHER PUBLICATIONS

International Search Report and Written Opinion for PCT/US2008/058414, dated Jul. 31, 2008, 7 pages.

* cited by examiner

*Primary Examiner* — Eric M Blount
(74) *Attorney, Agent, or Firm* — Armstrong Teasdale LLP

(57) ABSTRACT

An air monitoring apparatus includes, in an exemplary embodiment, a housing having at least one fluid passage to permit a fluid to enter the housing, and a constituent detection device positioned in the housing. The detection device includes at least one electrode, a power supply electrically coupled to the at least on electrode, and a logic circuit electrically coupled to the power supply. The logic circuit is configured to detect a change in at least one of impedance magnitude and a phase shift angle magnitude over a range of frequencies when the detection device contacts at least one fluid constituent contained in the fluid flowing into the cartridge through the at least one fluid passage, or when the detection device contacts at least one constituent in a solid whose chemical and/or material properties change as a function of fluid flowing into the housing through the at least one fluid passage.

18 Claims, 5 Drawing Sheets

US 8,089,367 B2

METHOD AND APPARATUS FOR DETECTING CONSTITUENT CHANGES IN AN ENVIRONMENT

CROSS REFERENCE TO RELATED APPLICATIONS

This application claims the benefit of Provisional Patent Application No. 60/908,563, filed Mar. 28, 2007, which is hereby incorporated by reference in its entirety.

BACKGROUND OF THE INVENTION

This invention relates generally to a sensor system capable of detecting constituent changes in characterized and unknown environments while discriminating non-relevant environmental changes, and specifically to utilizing such a sensor system within a respiratory protection apparatus.

Detecting potentially harmful constituents in gaseous environments, including air and other atmospheres, as well as in water and other liquids, can improve the safety of military combatants, emergency first responders, workers in industrial facilities, and the general public. Some known sensors developed for these purposes are configured to detect a single specific constituent. While many of these known sensors are sensitive to the constituent(s) of interest, they may also respond to other substances present, thereby either disguising a hazard associated with the constituent(s) of interest or inducing nuisance readings and alarms.

At least some other known sensors developed for these purposes are configured to detect a plurality of constituents. Many of these known sensors do not include a capacity to distinguish between each of the constituents of interest or a capacity to discriminate against constituents not of interest. Moreover, these known sensors do not include features that facilitate simultaneous detection of multiple substances coupled with providing responses specific to each constituent. Therefore, achieving detection and identification of multiple constituents often requires an increase in the number of sensors needed for such detections. Use of multiple sensors leads to increases in capital and maintenance costs associated with these sensor systems.

BRIEF DESCRIPTION OF THE INVENTION

In one aspect, an air monitoring apparatus is provided. The air monitoring apparatus includes a housing having at least one fluid passage to permit a fluid to enter the housing, and a constituent detection device positioned in the housing. The detection device includes at least one electrode, a power supply electrically coupled to the at least on electrode, and a logic circuit electrically coupled to the power supply. The logic circuit is configured to detect a change in at least one of impedance magnitude and a phase shift angle magnitude as a function of frequency when the detection device contacts at least one fluid constituent contained in the fluid flowing into the housing through the at least one fluid passage, or when the detection device contacts at least one constituent in a solid wherein at least one of chemical and material properties of the solid change as a function of fluid flowing into the housing through the at least one fluid passage.

In another aspect, a detection device for detecting constituents or constituent changes in a fluid or solid material is provided. The detection device includes at least one electrode, a power supply electrically coupled to the at least on electrode, and a logic circuit electrically coupled to the power supply. The logic circuit is configured to detect a change in at least one of impedance magnitude and a phase shift angle magnitude when the detection device contacts at least one fluid constituent contained in the fluid or solid.

In a further aspect, a method of detecting constituents in a fluid or solid is provided. The method includes providing a constituent detection device. The detection device includes at least one electrode, a power supply electrically coupled to the at least on electrode, and a logic circuit electrically coupled to the power supply. The logic circuit is configured to detect a change in at least one of impedance magnitude and a phase shift angle magnitude when the detection device contacts at least one constituent contained in the fluid or solid. The method also includes generating an AC signal having a predetermined frequency, a phase shift angle magnitude, a voltage magnitude, and an electric current magnitude, transmitting the AC signal through the at least one electrode and measuring at least one of an impedance, a phase shift angle, capacitance, and inductance as a function of the applied AC signal, positioning the at least one electrode in flow communications with a fluid source or in contact with a solid, and measuring any change in the impedance and the phase shift angle of the AC signal to determine if a constituent is present in the fluid or solid.

DETAILED DESCRIPTION OF THE INVENTION

A constituent detector device is described below in detail. One exemplary embodiment described below includes the constituent detector device in a respirator device. However, it should be understood that the constituent detector device can be used to detect constituents in a stand-alone mode in HVAC systems, in personal monitoring systems, on area monitoring systems, in liquids, and in solid phase materials, for example, carbon, zeolites, and dirt.

Figure 1:
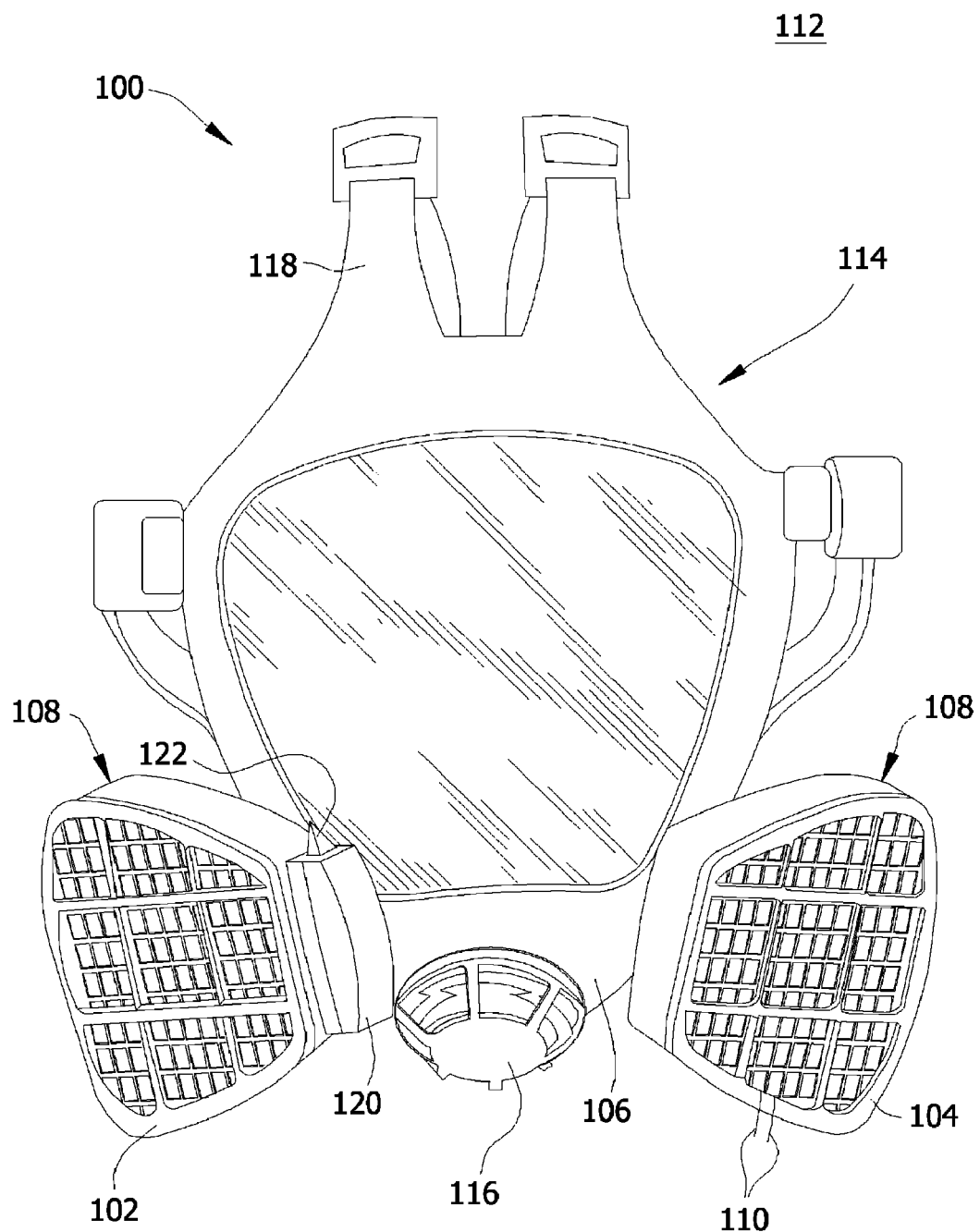
FIG. 1 is a schematic view of an exemplary respiratory protection apparatus in accordance with an embodiment of the present invention.

Referring to the drawings, FIG. 1 is a schematic view of an exemplary respiratory protection apparatus 100. Apparatus 100 includes a pair of air-purifying respirator cartridges 102 and 104 disposed laterally from a face mask 106. Outer surfaces 108 of cartridges 102 and 104 define a housing and contain a plurality of fluid passages 110 that are in flow communication with ambient air in the external environment 112. In the exemplary embodiment, passages 110 are configured to channel air. Alternatively, passages 110 are configured to channel any fluid including gases, for example, air, and liquids, for example, including water into cartridges 102 and 104.

Passages 110 extend through a sorbent material in cartridges 102 and 104 and into a face mask chamber 114, and facilitate fluid flow from environment 112 into chamber 114. In the exemplary embodiment, cartridge 102 is the same as cartridge 104. Alternatively, cartridge 102 and cartridge 104 have differing configurations. Apparatus 100 also includes an exhaust device 116 that facilitates air exhaled by the user to be exhausted into external environment 112. Apparatus 100 further includes an attaching device 118 for retaining face mask 106 on the face of the user.

The sorbent materials in cartridges 102 and 104 are configured to adsorb target constituents in the ambient air to provide fresh, breathable air to the user. The sorbent materials may be selected based on the target constituents and other design criteria, which are known in the art. Target constituents can be any molecular species in the air including the components of air. Some example constituents include, but are not limited to, chemical gases and/or vapors, biological agents, moisture vapor, explosives, radioactive particles and the like.

Apparatus 100 also includes an power supply 120 that is releasably coupled to cartridge housing 102. Power supply 120 is configured to generate an AC signal that includes a predetermined frequency, a first phase shift angle magnitude, a voltage magnitude, and a first electric current magnitude. Apparatus 100 also includes at least one constituent detection device 150 (shown in FIG. 2) that is embedded within the sorbent material and coupled in flow communication with at least one passage 110. Moreover, each detection device 150 is electrically coupled to power supply 120. Detection devices 150 are configured to monitor air, or other fluid, as it flows through at least a portion of the sorbent material as discussed further below. In another embodiment, detection device 150 is configured to detect constituents in solid material, for example the sorbent material, as the air or other fluid passes through the solid material. At least one indicator 122 is located on power source 120 so that indicator 122 is visible when attached to apparatus 100 as it is being worn by a user. It will be understood that exposure indicator 122 may be attached to either or both of cartridge housings 102 and 104.

In operation, a user wears apparatus 100 such that attaching device 118 securely holds face mask 106 against the user's face. The user breathes in air, or other fluid, from environment 112 and air is channeled into chamber 114 through passages 110 of the sorbent material within cartridges 102 and 104. Air flows by at least one constituent detection device 150 embedded within at least one of passages 110. As the user exhales, air is channeled thought exhaust device 116 into environment 112. Power source 120 transmits AC electric power to constituent detection devices 150 wherein detection devices 150 monitor the air within passages 110 for predetermined constituents. In the event that a predetermined concentration of the constituents being monitored are detected by detection devices 150, indicator 122 notifies the user.

Figure 2:
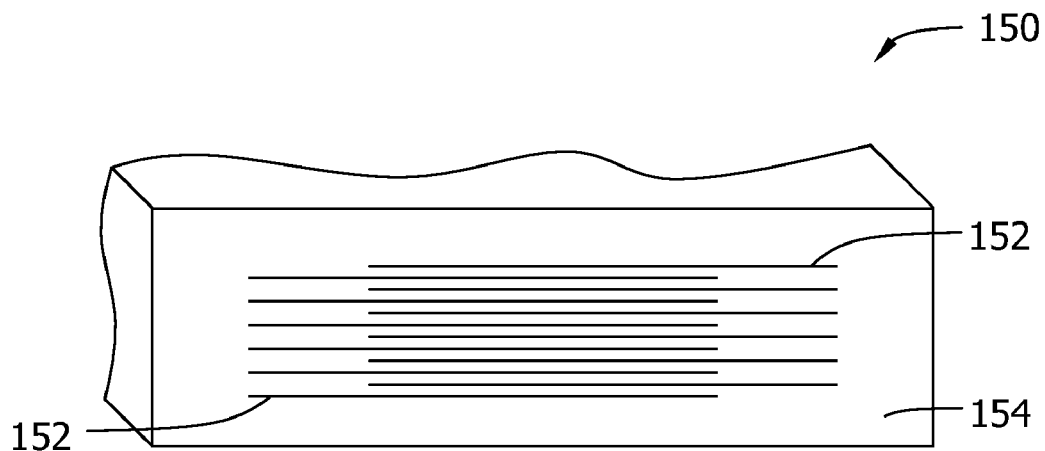
FIG. 2 is a perspective view of an exemplary constituent detection device in the respiratory protection apparatus shown in FIG. 1.
Figure 3:
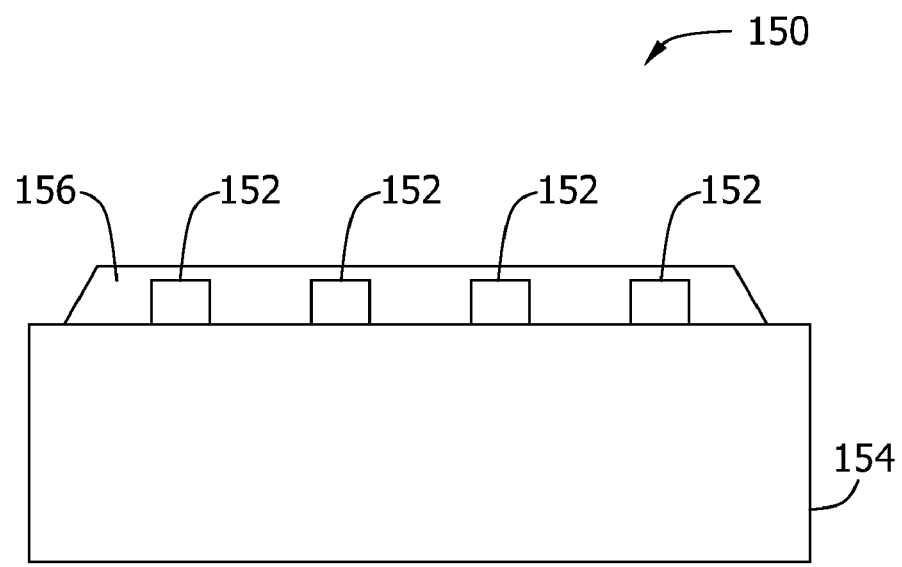
FIG. 3 is an end view of the constituent detection device shown in FIG. 2.

FIG. 2 is a perspective view of an exemplary constituent detection device 150 that may be used with respiratory protection apparatus 100 (shown in FIG. 1), and FIG. 3 is an end view of detection device 150. In the exemplary embodiment, detection device 150 is an electrode that includes a plurality of interdigitated micro-electrodes 152 positioned on a body 154. Any suitable micro-electrodes can be used, for example, micro-electrodes available from Synkera Technologies, Inc., Longmont, Colo. Body 154 can be formed from any suitable non-conductive material, for example, a ceramic material. A coating 156 is applied over micro-electrodes 152 and body 154. Coating 156 is formed from at least one material that includes, but is not limited to, a dye, organic ionic materials, inorganic ionic materials, conductive polymers, nonconductive polymers, cationic polymers, anionic polymers, inorganic sorbents, and small organic molecules. Coatings 156 can be thin films, gels, membranes, nanomaterials such as carbon nanotubes, colloids, and self-assembled layers, for example, solids such as carbon, zeolites, silicas, and the like. Coating 156 is engineered such that it responds in a defined frequency regime of a predetermined frequency spectrum to a stimulus provided by a single analyte or grouping of analytes. In the exemplary embodiment, a response to a stimulus includes, but is not limited to, a change in impedance magnitude and a change in phase shift angle magnitude and direction, as discussed further below.

In an alternate embodiment, detection device 150 includes two or more coatings 156 applied to electrodes 152. These coatings can be adjacent to each other in the same plane or can be applied as successive layers. Each coating is engineered such that it responds to a stimulus provided by a single analyte or grouping of analytes in a defined frequency regime of a predetermined frequency spectrum. In a further alternate embodiment, there is no coating on electrodes 152 of detection device 156. In another embodiment, detection device 150 is any dielectric device that facilitates operation of apparatus 100 as described herein.

In the exemplary embodiment, detection device 150 is positioned within apparatus 100. Alternatively, detection device 150 is positioned in any sensor system wherein such system's operation is facilitated by detection device 150. Such systems include, but are not limited to, ventilation systems (HVAC systems), personal monitoring devices, area monitoring devices, and liquids, for example, water supply systems. Also, detector device 150 can be used to detect constituent changes in solid phase materials, for example, carbon, zeolites, dirt, and the like.

Figure 4:
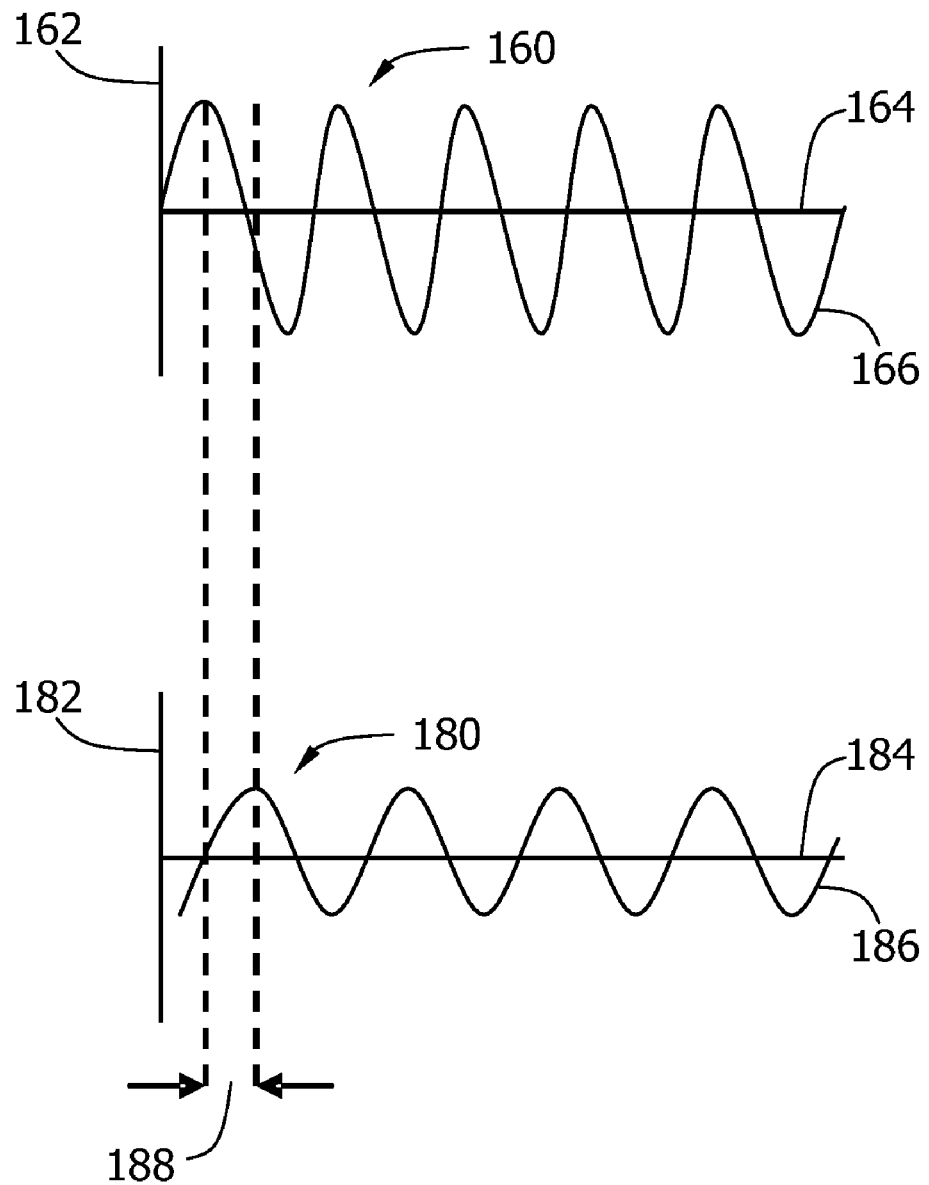
FIG. 4 is a graphical view of exemplary voltage and current signals associated with the constituent detection device shown in FIG. 2.

FIG. 4 includes two graphical views of an exemplary voltage signal and current signal, specifically, voltage signal graph 160 and current signal graph 180, respectively. Graphs 160 and 180 are general representations of electrical signals associated with constituent detection device 150 (shown in FIG. 2). Voltage signal graph 160 includes an ordinate (Y-axis) 162 and an abscissa (X-axis) 164. Ordinate 162 represents an amplitude, or magnitude, of a voltage signal 166 in predetermined increments. Abscissa 164 represents time in predetermined increments. Voltage signal 166 is generated by AC power source 120 (shown in FIG. 1) and transmitted to detection device 150. An amplitude, or magnitude, of voltage signal 166 may be represented by the following algorithm:

$$E_{appl}(t)=E_0*\cos(\omega t) \quad (1)$$

where the term $E_{appl}(t)$ represents the amplitude of applied voltage potential 166 as a function of time, $E_0$ represents a voltage potential at time (t), equals zero (0), and $\omega$ represents a predetermined frequency associated with AC signal 166.

Current signal graph 180 includes an ordinate (Y-axis) 182 and an abscissa (X-axis) 184. Ordinate 182 represents an amplitude, or magnitude, of a current signal 186 in predetermined increments. Abscissa 184 represents time in predetermined increments. Current signal 186 is induced within detection device 150 by voltage signal 166 generated by AC power source 120. An amplitude, or magnitude, of current signal 186 may be represented in the following algorithm:

$$I_{ind}(t)=I_0*\sin(\omega t-\theta) \quad (2)$$

where the term $I_{ind}(t)$ represents the amplitude of induced current 186 within detection device 150 as a function of time, $I_0$ represents a induced current at time (t), equals zero (0), ω represents a predetermined frequency associated with current signal 186, and θ represents a phase shift angle 188. Phase shift angle 188 is formed as a function of predetermined inductive and capacitive properties within detection device 150. In the exemplary embodiment, phase shift angle 188 is a lagging angle in that current signal 186 lags voltage signal 166. Alternatively, phase shift angle 188 includes any leading or lagging value that facilitates operation of detection device 150 as described herein.

Voltage signal 166 and current signal 186 are related by the following algorithm:

$$\text{Impedance}(Z) = E_{appl}(t) / I_{ind}(t) \quad (3)$$
$$= E_0 * \cos(\omega t) / I_0 * \sin(\omega t - \theta) \quad (4)$$

where Z represents an impedance of detection device 150 as discussed further below. Alternatively, algorithm (4) may be expressed as:

$$Z * I_0 * \sin(\omega t - \theta) = E_0 * \cos(\omega t) \quad (5)$$

In operation, application of AC voltage signal 166 ($E_{appl}$) to electrodes 152 within detection device 150 induces an alternating current signal 186 ($I_{ind}$) in detection device 150 which is different in magnitude (at least partially due to the impedance (Z) of the material as shown in algorithm (5)) and phase shifted by angle 188 relative to voltage signal 166. As illustrated in algorithm (4), the ratio of voltage signal 166 to induced current signal 186 defines impedance Z, of the material of detection device 150 including the electrodes, the base, and the coating. The impedance is at least partially based upon an electrical resistance to current flow, an inductive reactance and a capacitive reactance, wherein such resistances and reactances are inherent characteristics of the materials under consideration. The values of the instantaneous reactances are functions of the instantaneous frequency of the electrical signals being transmitted through the material. Substantially all materials demonstrate similar general characteristics, and the shift in magnitude and phase angle tends to be more pronounced at certain resonant frequencies, wherein such resonant frequencies vary and are specific for different materials. For a given material with a defined impedance magnitude and phase shift angle 188 at a specified resonant frequency (ω) of voltage signal 166, subtle changes in the inherent magnitude and phase shift angles 188 can be used to sense an external force (not shown) acting on the material such as those forces discussed further below.

Detection device 150 leverages the principles of electrochemical impedance spectroscopy (EIS) to facilitate operation of detection device 150 as disclosed herein. EIS is a technique that may be used to analyze activities that include, but are not limited to, polymer curing phenomena, corrosion of metal surfaces and coatings, and prediction of polymer failure modes in critical applications such as oil rig piping. The fundamental principle of this technique focuses on small changes in the ability of a material to resist flow of electrical current (that is, the material's impedance (Z)) that can be used for nonconductive, for example, dielectric, and conductive materials. AC voltage EIS is generally the preferred method for use with dielectric materials because the application of small AC voltage and current signals induces very subtle changes in the impedance of those materials due to external forces that can be detected as the material properties change. These external forces include, but are not limited to, corrosion, moisture adsorption, and chemical reactions. Such external forces may be induced by ionic reactions between predetermined fluid constituents and materials within detection device 150.

As discussed above, there is a frequency dependence of the impedance and phase response due to analyte(s) that can be tuned by the use of materials that include, but are not limited to, dyes, organic and inorganic ionic materials, conductive and nonconductive polymers, cationic and anionic polymers, inorganic sorbents, and small organic molecules. A phase response due to analyte(s) can change in a positive or negative direction depending on the interaction of the materials of detection device 150 and the analyte(s). These characteristics are used in conjunction with other characteristics to impart analyte-differentiating capability to detection device 150, wherein such other characteristics include, but are not limited to, the frequency-dependent impedance and phase shift.

Detection device 150 is configured to facilitate detection of constituents in air and other atmospheres. Detecting potentially harmful constituents in air and other atmospheres, as well as water and other liquids, facilitates the safety of military combatants, emergency first responders, workers in industrial facilities, and the general public. Detection device 150 may be configured to be sensitive to one constituent of interest such that it detects a single specific constituent while mitigating responses to other substances present. Such configuration facilitates reducing nuisance readings and alarms. Moreover, detection device 150 may be configured to detect a plurality of constituents. Detection device 150 includes a capacity to distinguish between constituents of interest from each other as well as from constituents not of interest Also, in one embodiment, detection device 150 has the capacity to quantify the amount of a constituent. Detection device 150 includes features that facilitate simultaneous detection of multiple substances coupled with providing responses specific to each constituent. Therefore, detection device 150 facilitates detection and identification of multiple constituents without necessitating an increase in the number of sensors.

Specifically, detection device 150 facilitates detection of any substance, regardless of its chemical makeup, that is not expected to be present in a given environment. For example, within a given atmosphere the background constituents might be elements of air. Alternatively, the background constituents are elements of air and other known substances which are expected to be present. Further, alternatively, the background constituents of the atmosphere are purely synthetic in nature, wherein the constituents and the atmosphere have been created artificially for a designated purpose. In any instance, detection device 150 facilitates detection of changes of a predetermined magnitude in the atmosphere relative to background constituents. Moreover, detection device 150 is configured to detect any substance except those that are expected to be present in the background atmosphere. Furthermore, detection device 150 is configured for specific atmospheric formulations such that extraneous substances, if present, could be detected over background in a substantially short period of time.

For example, water or water vapor can uniquely affect ions and ionic movement in solid formulations. In the context of the AC impedance spectrum, ionic content will tend to manifest itself at lower frequencies (10-50 kHz). The absence or presence of water will have a more pronounced effect in this frequency regime due to interactions of the water with ions. In the exemplary embodiment, detection device 150 is modified with customized formulations that facilitate sensitizing detection device 150 to moisture vapor relative to organics and more lipophilic compounds. Additionally, detection device 150 coating formulations containing chemical species that interact with organic chemical contaminants (species other than water) provide an impedance responsive to organics at higher frequencies where electronic interactions and inductive effects dominate. These organic contaminants are not expected to have any effect on ionic constituents.

Formulations are developed for sensitization of electrodes to moisture and to lipophilic compounds (chemical agents). In the exemplary embodiment, modification of detection device 150 with a particular material facilitates producing a single electrode sensor detection device 150 capable of monitoring both moisture and chemical contaminant content. Alternatively, a multiple material approach is used in which the response on each material's impedance will be compared with simple logic algorithms to differentiate water and chemical contaminants. Such materials include polymeric film-forming materials such as, but not limited to, NAFION® copolymer (a registered trademark of E.I. DuPont de Nemours brand of perfluorosulfonic acid/TFE copolymer), polyvinyl alcohol, polydimethylsiloxane, and blends thereof, and other materials, for example, ASZM-TEDA, zeolite, and silica.

Figure 5:
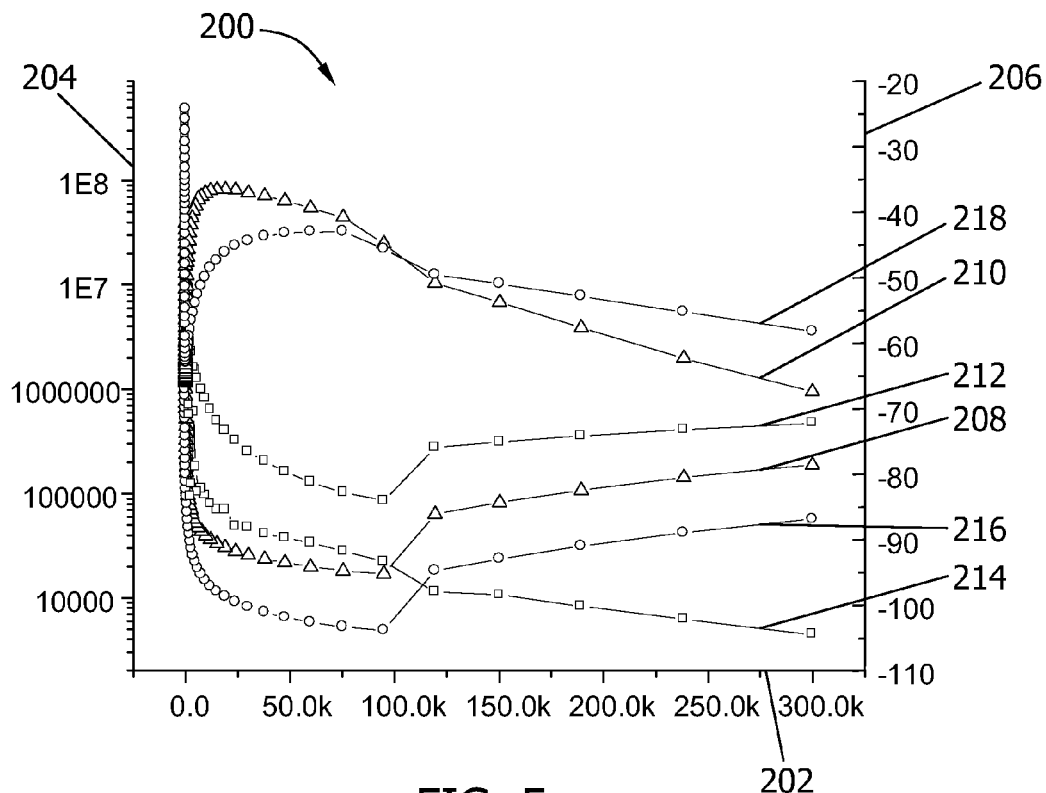
FIG. 5 is a graphical view of a plurality of electrical characteristics of an embodiment of the constituent detection device shown in FIG. 2.

FIG. 5 is a graphical view 200 of a plurality of electrical characteristics of a first embodiment of constituent detection device 150 (shown in FIG. 2). Graph 200 includes an abscissa (X-axis) 202 that represents frequency ($\omega$) in units of Hz. Abscissa 202 is linearly illustrated in 25 KHz increments from 0.0 kHz to 300.0 kHz. Graph 200 also includes a first ordinate (Y-axis) 204 that represents an impedance (Z) of detection device 150 in units of ohms ($\Omega$). Ordinate 204 is logarithmically illustrated from 1000% to $1*10^8 \Omega$. Graph 200 further includes a second ordinate (Y-axis) 206 that represents phase shift angle ($\theta$) in units of degrees. Ordinate 206 is linearly illustrated from −110 degrees to −20 degrees.

In this first embodiment, detection device 150 includes at least one layer of a NAFION® copolymer film formed over interdigitated electrodes 152 (shown in FIG. 2). Graph 200 includes a curve 208 that represents impedance (Z) of detection device 150 over a frequency range of 1.0 kHz to 300.0 kHz while immersed in an atmosphere substantially formed of ambient air. Graph 200 also includes a curve 210 that represents phase shift angle ($\theta$) 188 of current signal 186 (both shown in FIG. 3) being transmitted through detection device 150 over a frequency range of 1.0 kHz to 300.0 kHz while immersed in an atmosphere substantially formed of ambient air. Curves 208 and 210 are illustrated for reference.

Graph 200 further includes a curve 212 that represents impedance (Z) of detection device 150 over a frequency range of 1.0 kHz to 300.0 kHz while immersed in an atmosphere substantially formed of dichloromethane (DCM) vapor. Graph 200 also includes a curve 214 that represents phase shift angle ($\theta$) 188 of current signal 186 being transmitted through detection device 150 over a frequency range of 1.0 kHz to 300.0 kHz while immersed in an atmosphere substantially formed of DCM vapor.

Graph 200 further includes a curve 216 that represents impedance (Z) of detection device 150 over a frequency range of 1.0 kHz to 300.0 kHz while immersed in an atmosphere substantially formed of water vapor. Graph 200 also includes a curve 218 that represents phase shift angle ($\theta$) 188 of current signal 186 being transmitted through detection device 150 over a frequency range of 1.0 kHz to 300.0 kHz while immersed in an atmosphere substantially formed of water vapor.

As can be seen in graph 200, the magnitudes of the coating's Z as a function of exposure to DCM vapor (curve 212) versus water vapor (curve 216) differ substantially. However, the changes in magnitude of the coating's Z as a function of exposure to DCM vapor (curve 212) and water vapor (curve 216) are similar to each other across the illustrated frequency spectrum. Curve 214, corresponding to DCM vapor, indicates a significant and substantially uniform negative change in $\theta$ across the illustrated frequency spectrum when this first embodiment for detection device 150 is exposed to DCM vapor. In contrast, curve 218 indicates an initial sharp increase and then a significant and substantially uniform negative change in $\theta$ across the illustrated frequency spectrum indicating that water vapor has little effect on $\theta$ at the opposite ends of the frequency spectrum for this first embodiment of detection device 150.

Figure 6:
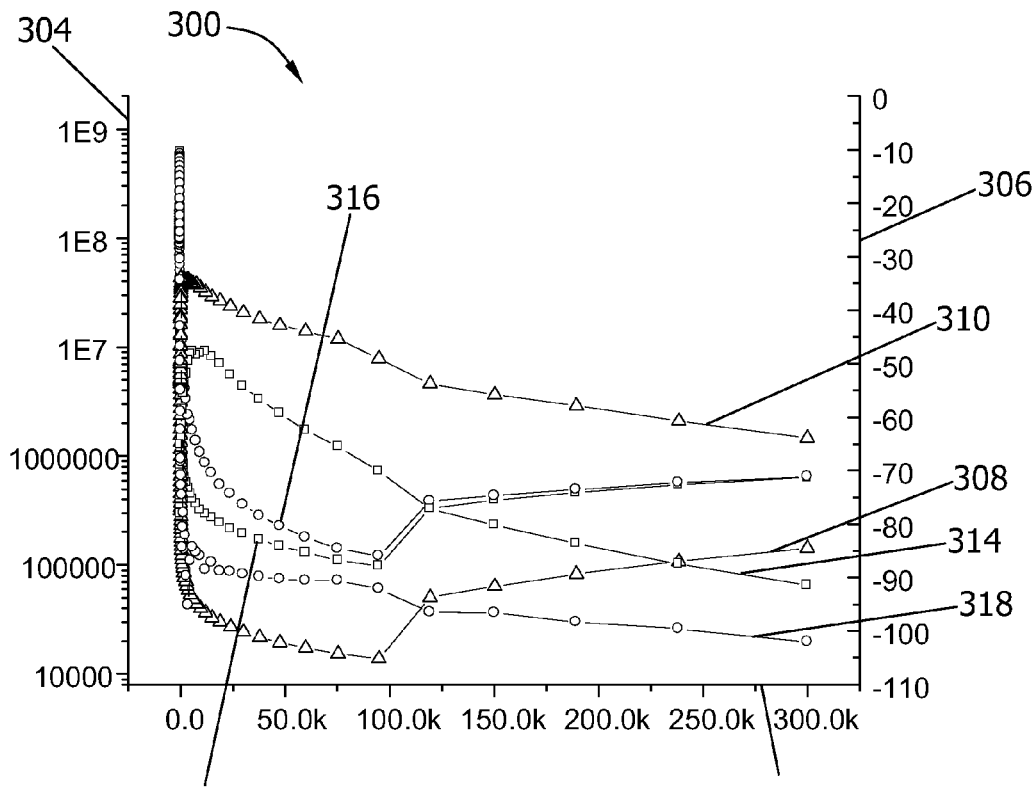
FIG. 6 is a graphical view of a plurality of electrical characteristics of another embodiment of the constituent detection device shown in FIG. 2.

FIG. 6 is a graphical view 300 of a plurality of electrical characteristics of a second embodiment of constituent detection device 150 (shown in FIG. 2). Graph 300 includes an abscissa (X-axis) 302 that represents frequency ($\omega$) in units of Hz. Abscissa 302 is linearly illustrated in 25 KHz increments from 0.0 kHz to 300.0 kHz. Graph 300 also includes a first ordinate (Y-axis) 304 that represents an impedance (Z) of detection device 150 in units of ohms ($\Omega$). Ordinate 304 is logarithmically illustrated from 10,000$\Omega$ to $1*10^9 \Omega$. Graph 300 further includes a second ordinate (Y-axis) 306 that represents phase shift angle ($\theta$) in units of degrees (°). Ordinate 306 is linearly illustrated from −110° to 0°.

In this second embodiment, detection device 150 includes at least one layer of a NAFION® copolymer film with interspersed potassium ions ($K^+$) formed over interdigitated electrodes 152 (shown in FIG. 2). The potassium ions are embedded within the NAFION® copolymer film by immersing the NAFION® copolymer film in an aqueous potassium hydroxide (KOH) solution for a predetermined period of time. Subsequently, the KOH-soaked NAFION® copolymer film is oven-dried at approximately 70° C. (158° F.). Graph 300 includes a curve 308 that represents impedance (Z) of detection device 150 over a frequency range of 1.0 kHz to 300.0 kHz while immersed in an atmosphere substantially formed of ambient air. Graph 300 also includes a curve 310 that represents phase shift angle ($\theta$) 188 of current signal 186 (both shown in FIG. 3) being transmitted through detection device 150 over a frequency range of 1.0 kHz to 300.0 kHz while immersed in an atmosphere substantially formed of ambient air. Curves 308 and 310 are illustrated for reference.

Graph 300 further includes a curve 312 that represents impedance (Z) of detection device 150 over a frequency range of 1.0 kHz to 300.0 kHz while immersed in an atmosphere substantially formed of dichloromethane (DCM) vapor. Graph 300 also includes a curve 314 that represents phase shift angle ($\theta$) 188 of current signal 186 being transmitted through detection device 150 over a frequency range of 1.0 kHz to 300.0 kHz while immersed in an atmosphere substantially formed of DCM vapor.

Graph 300 further includes a curve 316 that represents impedance (Z) of detection device 150 over a frequency range of 1.0 kHz to 300.0 kHz while immersed in an atmosphere substantially formed of water vapor. Graph 300 also includes a curve 318 that represents phase shift angle ($\theta$) 188 of current signal 186 being transmitted through detection device 150 over a frequency range of 1.0 kHz to 300.0 kHz while immersed in an atmosphere substantially formed of water vapor.

Graph 300 illustrates little change in the Z and $\theta$ responses between the $K^+$-impregnated NAFION® copolymer film (curves 308 and 310, respectively, shown in FIG. 4) and the non-impregnated NAFION® copolymer film (curves 208 and 210, respectively, shown in FIG. 4).

As can be seen in graph 300, the magnitude of the coating's impedance Z as a function of exposure to DCM vapor (curve 312) and water vapor (curve 316) are substantially similar to each other. Curves 312 and 316 illustrate that the magnitude of the coating's impedance Z substantially changes between 1.0 kHz and 50 kHz while there is only a small change above 50 kHz. Moreover, the changes in magnitude of the coating's impedance Z as a function of exposure to DCM vapor (curve 312) and water vapor (curve 316) are similar to each other across the illustrated frequency spectrum. A contrast between the general shape of curves 312 and 316 and curves 212 and 216 (shown in FIG. 5), respectively, indicates a substantial difference of the impedance Z responses between the $K^+$-impregnated NAFION® copolymer film and the non-impregnated NAFION® copolymer film.

Curve 314 is similar to curve 214 (shown in FIG. 5) in that curve 314 indicates a significant and substantially uniform negative change in θ across the illustrated frequency spectrum when this second embodiment for detection device 150 is exposed to DCM vapor. In contrast, a general shape of curve 318 is dissimilar to a general shape of curve 218 (shown in FIG. 5). Curve 318 indicates an initial sharp decrease and then a significant and substantially uniform negative change in θ across the illustrated frequency spectrum indicating that water vapor has a substantially different effect on θ between the first and second embodiments of detection device 150. The differing phase responses to water moisture suggests that it is possible to sensitize the detection device 150 to facilitate differentiating moisture responses from chemical contaminant responses.

Alternative methods of differentiating moisture responses from chemical contaminant responses include using polycationic polymer films. Such films may be 1000 times more conductive when taken from substantially dry conditions to approximately 90% relative humidity (RH) levels. At least some spectroscopic studies suggest that long range directional dependence, or anisotropy, of these materials imparts additional conductivity in the plane of the film. Further alternative methods include humidity sensors based on NAFION®-crystal violet films. This method uses water uptake which facilitates ionization of dye and polymer, thereby producing an optical response in response to humidity. This optical response is a result of a change in the electronic structure of the dye and hence a change in band gap. At least some of these optical changes may be associated with, and more sensitively monitored by, complex impedance measurements.

Figure 7:
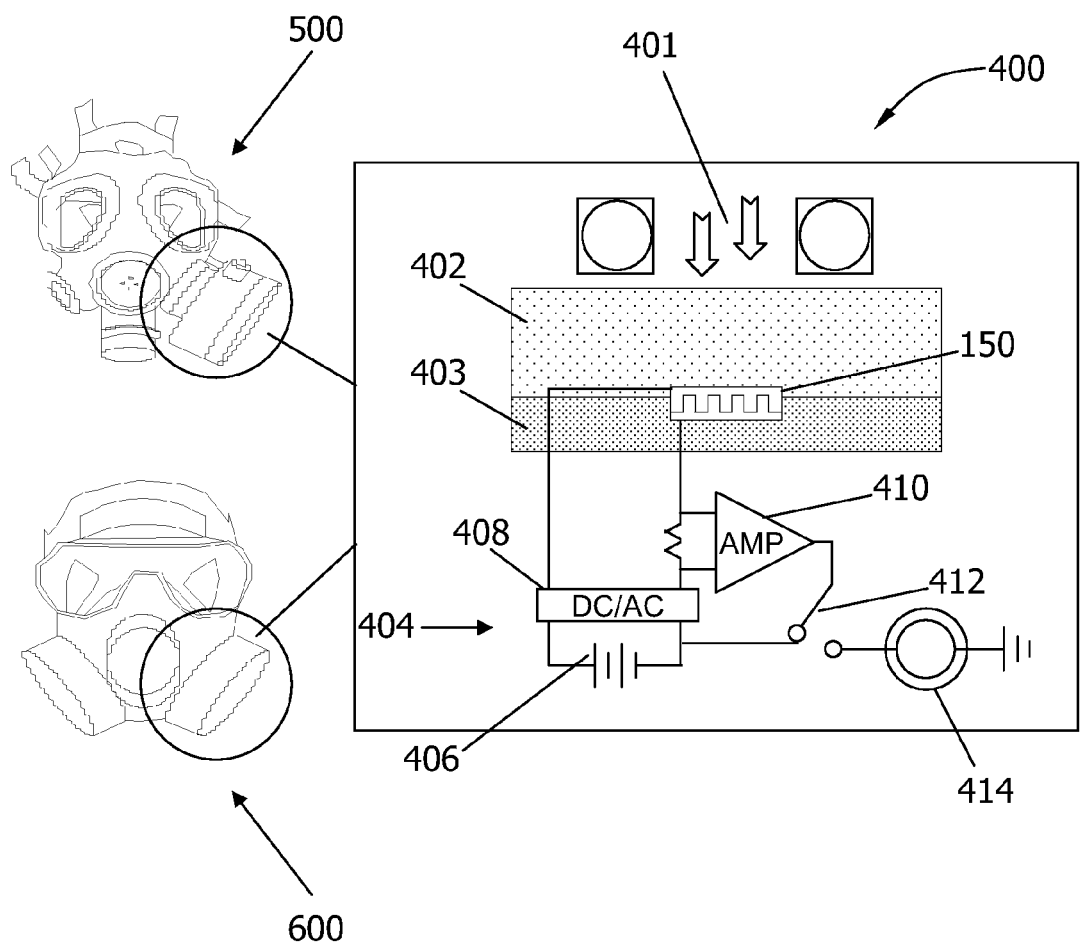
FIG. 7 is a schematic view of an exemplary contaminant detection system embedded in the respiratory protection apparatus shown in FIG. 1.

FIG. 7 is a schematic view of an exemplary contaminant detection system 400 embedded in a plurality of respiratory protection apparatus 500 and 600. System 400 is configured to receive an air stream 401. System 400 includes detection device 150 positioned at a specified depth within a layer of filter media 402 and a residual protective media layer 403. In the exemplary embodiment, filter 402 is formed with absorbent carbon. Alternatively, filter 402 is any material that facilitates operation of system 400 as described herein. Layers 402 and 403 are positioned within each of a carbon-based air purifying respiratory protection apparatus 500 and 600 where minute impedance changes due to adsorption of chemical and biological agents can be monitored.

System 400 also includes a power source 404 that is electrically coupled to detection device 150. In the exemplary embodiment, power source 404 includes a battery 406 and a direct current (DC)-to-AC converter 408. System 400 further includes a logic circuit 410 electrically coupled to power source 402. In the exemplary embodiment, logic circuit 410 is one operational amplifier (op-amp) configured to detect changes in current signal 186 (shown in FIG. 2) as a function of a change in Z. Alternatively, logic circuit 410 is any configuration of circuitry and soft logic that facilitates operation of system 400 as described herein. System 400 also includes a switch 412 electrically coupled to circuit 410 and power source 404. In the exemplary embodiment, switch 412 is a physical switching device configured to shift position as a function of commands received from circuit 410. Alternatively, switch 412 includes any electronic and soft logic configuration that facilitates operation of system 400 as described herein. System 400 further includes an alarm 414 electrically coupled to power source 404 and switch 412. In the exemplary embodiment, alarm 414 is a light emitting diode. Alternatively, alarm 414 is any device that facilitates operation of system 400 as described herein including, but not limited to, a locally audible device, a vibratory device, an alphanumeric display device, a symbolic display device, and a wireless transmitter.

An exemplary method of detecting constituents in a fluid is provided. The method includes generating an AC signal with a predetermined frequency, a phase shift angle magnitude 188, a voltage magnitude 166, and an electric current magnitude 186 (shown in FIG. 4). The method also includes transmitting the AC signal through at least one coating material, wherein the coating material includes an impedance Z. The method further includes placing the at least one coating material in flow communication with at least one fluid source 401 that includes at least one constituent being monitored for detection. The method also includes determining whether there is a change in at least one of the impedance Z and phase shift angle magnitude 188. The coating material can be a dielectric material or a material other than a dielectric material.

In operation, simultaneous monitoring of moisture content can be carried out and this data can be correlated with expected performance of the cartridge against chemical agents of interest. Circuit 410 is used to monitor for these changes and to provide a warning signal via device 414 when a predefined threshold of change in impedance has occurred. This threshold change is induced by adsorption of chemical and biological materials on the carbon and is thus non-specific in nature. Moisture in this case is an expected contaminant in the atmosphere and while it is important to understand the level of moisture in the carbon sorbent, it is undesirable to alarm that moisture is present. Thus, the sensor monitors for constituent changes in the atmosphere surrounding the carbon relative to the expected atmosphere with perhaps dynamic levels of moisture vapor. These changes in filter 402 are directly related to the presence of adsorbed agent(s). Proper depth placement of detection device 150 in filter 402 then determines the amount of safety buffer (residual life) the user can rely on. In this way, the user requires no knowledge of the agent ID/concentration, environmental conditions, or history of the cartridge and can operate more safely and effectively without having to think about change-out schedules. Additionally, cost savings will be an added benefit of this technology since filter 402 is only thrown away when it is actually exhausted. The reusable, low-power device warns the user when to change out the cartridge.

The methods and apparatus for detecting constituent changes described above, facilitate detection of harmful constituents in air and other atmospheres. Detecting potentially harmful constituents in air and other atmospheres, as well as water and other liquids, facilitates the safety of workers in industrial facilities, military combatants, emergency first responders, and the general public. Specifically, the exemplary embodiment of detection device 150 may be configured to be sensitive to one constituent of interest such that it detects a single specific constituent while mitigating responses to other substances present. Such configuration facilitates reducing nuisance readings and alarms. Moreover, detection device 150 may be configured to detect a plurality of constituents. Specifically, detection device 150 includes a capacity to distinguish between constituents of interest from each other as well as from constituents not of interest. More specifically, detection device 150 includes features that facilitate simultaneous detection of multiple substances coupled with providing responses specific to each constituent. Therefore, detection device 150 facilitates detection and identification of multiple constituents without necessitating an increase in the number of sensors. Such reliance on a single detector leads to decreases in capital and maintenance costs of associated apparatus and sensors.

Exemplary embodiments of constituent detection as associated with respiratory protection apparatus are described above in detail. The methods, apparatus and systems are not limited to the specific embodiments described herein nor to the specific illustrated respiratory protection apparatus.

While the invention has been described in terms of various specific embodiments, those skilled in the art will recognize that the invention can be practiced with modification within the spirit and scope of the claims.

What is claimed is:

1. An air monitoring apparatus comprising:
   a housing, said housing comprising at least one fluid passage to permit a fluid to enter said housing; and
   a constituent detection device positioned in said housing, said detection device comprising:
      at least one electrode positioned on a body;
      at least one coating applied onto said at least one electrode and said body forming a film covering said at least one electrode and said body, said at least one coating comprising at least one material selected from the group consisting of, a dye, organic ionic materials, inorganic ionic materials, conductive polymers, nonconductive polymers, cationic polymers, anionic polymers, inorganic sorbents, and small organic molecules;
   a power supply electrically coupled to said at least on electrode, said power supply configured to generate an AC signal; and
   a logic circuit electrically coupled to said power supply, said logic circuit configured to detect a change in at least one of impedance magnitude and a phase shift angle magnitude as a function of applied frequency when said detection device contacts at least one fluid constituent contained in the fluid flowing into said housing through said at least one fluid passage or when said detection device contacts at least one constituent in a solid wherein at least one of chemical and material properties of the solid change as a function of fluid flowing into said housing through said at least one fluid passage.

2. An air monitoring apparatus in accordance with claim 1 further comprising an alarm mechanism coupled to said logic circuit.

3. An air monitoring apparatus in accordance with claim 2 wherein said alarm mechanism comprises at least one of a light device, an audible device, a vibratory device, an alphanumeric display device, a symbolic display device, and a wireless transmitter.

4. An air monitoring apparatus in accordance with claim 1 wherein said logic circuit comprises an operational amplifier configured to detect changes in a current signal as a function of a change in impedance magnitude.

5. An air monitoring apparatus in accordance with claim 1 wherein said base comprises a non-conductive material.

6. An air monitoring apparatus in accordance with claim 1 wherein said at least one electrode comprises a plurality of interdigitated electrodes.

7. An air monitoring apparatus in accordance with claim 1 wherein said detection device identifies and quantifies changes in constituents.

8. A detection device for detecting constituents or constituent changes in a fluid or a solid material, said detection device comprising:
   at least one electrode positioned on a body;
   at least one coating applied onto said at least one electrode and said body forming a film covering said at least one electrode and said body, said at least one coating comprising at least one material selected from the group consisting of, a dye, organic ionic materials, inorganic ionic materials, conductive polymers, nonconductive polymers, cationic polymers, anionic polymers, inorganic sorbents, and small organic molecules;
   a power supply electrically coupled to said at least on electrode, said power supply configured to generate an AC signal; and
   a logic circuit electrically coupled to said power supply, said logic circuit configured to detect a change in at least one of impedance magnitude and a phase shift angle magnitude when said detection device contacts at least one fluid constituent contained in a fluid or in a solid.

9. A detection device in accordance with claim 8 further comprising an alarm mechanism coupled to said logic circuit.

10. A detection device in accordance with claim 9 wherein said alarm mechanism comprises at least one of a light device, an audible device, vibratory device, an alphanumeric display device, a symbolic display device, and a wireless transmitter.

11. A detection device in accordance with claim 8 wherein said logic circuit comprises an operational amplifier configured to detect changes in a current signal as a function of a change in impedance magnitude.

12. A detection device in accordance with claim 8 wherein said base comprises a non-conductive material.

13. A detection device in accordance with claim 8 wherein said at least one electrode comprises a plurality of interdigitated electrodes.

14. A detection device in accordance with claim 8 wherein said detection device identifies and quantifies changes in constituents.

15. A method of detecting constituents in a fluid or a solid, said method comprising:
   providing a constituent detection device, the detection device comprising:
      at least one electrode positioned on a body;
      at least one coating applied onto the at least one electrode and the body forming a film covering said at least one electrode and said body, said at least one coating comprising at least one material selected from the group consisting of, a dye, organic ionic materials, inorganic ionic materials, conductive polymers, nonconductive polymers, cationic polymers, anionic polymers, inorganic sorbents, and small organic molecules;
      a power supply electrically coupled to the at least on electrode, the power supply configured to generate an AC signal; and
      a logic circuit electrically coupled to said power supply, said logic circuit configured to detect a change in at least one of impedance magnitude and a phase shift angle magnitude when said detection device contacts at least one fluid constituent contained in the fluid or solid;

generating an AC signal having a predetermined frequency, a phase shift angle magnitude, a voltage magnitude, and an electric current magnitude;

transmitting the AC signal through the at least one electrode and measuring an impedance and a phase shift angle of the AC signal;

positioning the at least one electrode in flow communications with a fluid source or in contact with a solid; and measuring any change in at least one of the impedance and the phase shift angle of the AC signal to determine if a constituent is present in the fluid or solid.

16. A method in accordance with claim 15 wherein the base comprises a non-conductive material.

17. A method in accordance with claim 15 wherein the at least one electrode comprises a plurality of interdigitated electrodes.

18. A method in accordance with claim 15 wherein the detection device identifies the constituent and quantifies the amount of the constituent.

* * * * *